United States Patent
Bharate et al.

(10) Patent No.: US 10,202,326 B2
(45) Date of Patent: Feb. 12, 2019

(54) POLYPRENYLATED PHLOROGLUCINOL COMPOUNDS AS POTENT P-GLYCOPROTEIN INDUCERS

(71) Applicant: COUNCIL OF SCIENTIFIC & INDUSTRIAL RESEARCH, New Delhi (IN)

(72) Inventors: Sandip Bharate, Jammu (IN); Ajay Kumar, Jammu (IN); Jaideep Bharate, Jammu (IN); Prashant Joshi, Jammu (IN); Abubakar Wani, Jammu (IN); Ramesh Mudududdla, Jammu (IN); Rohit Sharma, Jammu (IN); Ram Vishwakarma, Jammu (IN)

(73) Assignee: COUNCIL OF SCIENTIFIC & INDUSTRIAL RESEARCH, New Delhi (IN)

( * ) Notice: Subject to any disclaimer, the term of this patent is extended or adjusted under 35 U.S.C. 154(b) by 0 days.

(21) Appl. No.: 15/520,063

(22) PCT Filed: Jul. 20, 2015

(86) PCT No.: PCT/IN2015/050069
§ 371 (c)(1),
(2) Date: Apr. 18, 2017

(87) PCT Pub. No.: WO2016/063296
PCT Pub. Date: Apr. 28, 2016

(65) Prior Publication Data
US 2017/0320802 A1    Nov. 9, 2017

(30) Foreign Application Priority Data
Oct. 21, 2014 (IN) .......................... 3004/DEL/2014

(51) Int. Cl.
| | |
|---|---|
| C07C 205/34 | (2006.01) |
| A61K 31/122 | (2006.01) |
| C07C 49/743 | (2006.01) |
| C07C 49/84 | (2006.01) |
| C07D 311/96 | (2006.01) |

(52) U.S. Cl.
CPC ............ *C07C 49/84* (2013.01); *A61K 31/122* (2013.01); *C07C 49/743* (2013.01); *C07C 205/34* (2013.01); *C07D 311/96* (2013.01); *C07C 2603/56* (2017.05); *C07C 2603/70* (2017.05)

(58) Field of Classification Search
CPC ..... C07C 49/84; C07C 49/743; C07C 204/34; C07C 2603/56; C07C 2603/70; C07D 311/96; A61K 31/122
See application file for complete search history.

(56) References Cited

PUBLICATIONS

Delphine et al., 63(8) J. Nat. Prods. 1070-1076 (2000) (CAS Abstract) (Year: 2000).*
Murakami & Irie, 10 Proceedings of the Imperial Academy (Tokyo) 568-71 (1934) (CAS Abstract) (Year: 1934).*

* cited by examiner

*Primary Examiner* — Timothy R Rozof
(74) *Attorney, Agent, or Firm* — Foley & Lardner LLP (57) ABSTRACT

The present invention relates to the polyprenylated phloroglucinol compounds of formulae I and II. The present invention also provides synthesis and p-glycoprotein induction activity of the alkyl- and acyl-polyprenylated phloroglucinol compounds. Further, use of the compounds as p-glycoprotein inducers and methods of treatment of Alzheimer's disease using compounds of the invention are also provided.

10 Claims, 3 Drawing Sheets

POLYPRENYLATED PHLOROGLUCINOL COMPOUNDS AS POTENT P-GLYCOPROTEIN INDUCERS

CROSS-REFERENCE TO RELATED APPLICATIONS

The present application is a U.S. National Phase Application of International Patent Application No. PCT/IN2015/050069, filed Jul. 20, 2015, which claims priority to Indian Patent Application No. 3004/DEL/2014, filed Oct. 21, 2014, the entireties of which are incorporated herein by reference.

FIELD OF THE INVENTION

The present invention relates to the chemical compounds in general. More specifically, the present invention describes polyprenylated phloroglucinol compounds as potent P-glycoprotein inducers. The present invention also provides synthesis and p-glycoprotein induction activity of polyprenylated alkyl-phloroglucinol and polyprenylated acyl-phloroglucinol compounds.

BACKGROUND OF THE INVENTION

Alzheimer's disease is the most common form of senile dementia and the fourth highest cause of disability and death in the elderly. It is characterized by the presence of three main brain hallmarks viz. diffuse neuronal loss with a particular involvement of the cholinergic system, extracellular protein deposits (amyloid-beta plaques) and intracellular protein deposits (neurofibrillary tangles, NFTs). All current therapies are based on the cholinergic hypothesis and demonstrate only symptomatic treatment. Progression of the disease is not slowed or halted, with symptoms continuing to deteriorate over time. The amyloid hypothesis proposes that Alzheimer's disease is caused by an imbalance between Aβ production and clearance, resulting in increased amounts of Aβ in various forms such as monomers, oligomers, insoluble fibrils and plaques in the CNS. The rate of Aβ production is same as that in healthy volunteers; whereas rate of clearance is impaired by 25-30%. The high levels of Aβ then initiates the cascade of events culminating in neuronal damage and death manifesting as progressive dementia of the Alzheimer's disease type. Evidence shows that insufficient clearance of the Aβ protein from the brain is a prime cause in over 95% of Alzheimer's disease patients (Mawuenyega, K. G. et al. *Science* 2010, 330, 1774). Further, it is known that Aβ efflux is mediated by p-glycoprotein efflux pump. The p-glycoprotein deficiency at the blood brain barrier increases Aβ deposition in an Alzheimer's disease (Cirrito, J. R. et al., *J. Clin. Invest.* 2005, 115, 3285). P-glycoprotein (Pgp) is highly expressed on the luminal surface of brain capillary endothelial cells and contributes to the BBB. In Pgp-null mice, [$^{125}$I]-Aβ40 and [$^{125}$I]-Aβ42 microinjected into the CNS clear at half the rate than in WT mice. When amyloid precursor protein-transgenic (APP-transgenic) mice were administered Pgp inhibitor, Aβ levels within the brain interstitial fluid significantly increased within hours of treatment. APP-transgenic, Pgp-null mice had increased levels of brain Aβ and enhanced Aβ deposition compared with APP-transgenic, Pgp WT mice. These reports indicate a direct link between Pgp and Aβ metabolism in vivo and suggest that Pgp activity at the BBB could affect risk for developing Alzheimer's disease as well as provide a novel diagnostic and therapeutic target (Lam, F. C. et al., *J. Neurochem.* 2001, 76, 1121). Thus, it is evident that drugs that have ability to increase levels of Pgp should increase amyloid-beta clearance.

Phloroglucinols widely occur in nature in various plants including plants of Myrtaceae family. Colupulone, a tri-prenylatated acylphloroglucinol compound isolated from *Humulus lupulus* (Hops) is reported to display potent PXR activation activity. Another compound of this class, hyperforin isolated from *Hypericum perforatum* (St. John's Wort) also possess potent PXR activation and Pgp-induction activity. Garcinol (1a) and isogarcinol (2a) are polyprenylated phloroglucinol compounds isolated from Indian medicinal plant *Garcinia indica* (Rao, A. V. R et al., *Tetrahedron Lett.* 1980, 21, 1975; Krishnamurthy, N. and Ravindranath, B. *Tetrahedron Lett.* 1982, 23, 2233). A wide range of pharmacological activities (including anticancer, antiinflammatory, etc) have been reported for *Garcinia indica* as well as its chemical constituents (Tosa, H. et al., *Chem. Pharm. Bull.* 1997, 45, 418; Rukachaisirikul, V. et al., *Chem. Pharm. Bull.* 2005, 53, 342; Pan, M. H. et al., *J. Agric. Food Chem.* 2001, 49, 1464; Koeberle, A. et al., *Biochem. Pharmacol.* 2009, 77, 1513; Tian, Z. et al., *PLoS One* 2011, 6, e21370); however they are never been evaluated as Pgp inducers. In the present invention, the inventors disclose a new series of polyprenylated alkyl and acyl-phloroglucinol compounds as well as their activity as potent Pgp inducers. The novel compounds of the present invention exhibit potent Pgp activity and also do not show cytotoxicity.

Colupulone

Hyperforin

3a
Garcinol

4a
Isogarcinol wherein $R_1$ and $R_2$ group are individually selected from hydrogen, substituted or un-substituted alkyl group and substituted or un-substituted acyl group;

alkyl group is selected from the group comprising of methyl, ethyl, propyl, isopropyl, n-butyl, isobutyl, isovaleryl, propargyl, allyl, prenyl, geranyl, and other long aliphatic chains with chain length from $C_5$-$C_{20}$;

acyl group is selected from the group comprising of acetyl, benzyl, benzoyl and butanoyl.

OBJECTIVES OF THE INVENTION

The main object of the present invention is to provide polyprenylated alkyl-phloroglucinols and polyprenylated acyl-phloroglucinols. Another object of the present invention is to provide a method of synthesis of polyprenylated alkyl-phloroglucinols and polyprenylated acyl-phloroglucinols. Yet another object of the present invention is to provide treatment for Alzheimer's disease using compounds of the invention.

SUMMARY OF THE INVENTION

The present invention provides compounds represented by formulae I or II

DETAILED DESCRIPTION OF THE INVENTION

Accordingly, the present invention provides polyprenylated phloroglucinol compounds represented by general structures I and II as potent Pgp inducers.

I (1b)

3',4'-di-(O-butanoyl)-garcinol

II (1c)

3',4'-di-[O-(2'-iodo-benzyl)]-garcinol wherein, $R_1$ and $R_2$ group are individually selected from hydrogen, substituted or un-substituted alkyl or substituted or un-substituted acyl group, alkyl group is selected from a group comprising methyl, ethyl, propyl, isopropyl, n-butyl, isobutyl, isovaleryl, propargyl, allyl, prenyl, geranyl, and other long aliphatic chains with chain length from $C_5$-$C_{20}$; and acyl group is selected from a group comprising acetyl, benzyl, benzoyl and butanoyl group.

In one embodiment of the invention, the substitution on the alkyl or the acyl group is at one or more positions and selected from the group comprising of chloro, fluoro, iodo, and nitro.

In yet another embodiment, the benzyl group is selected from group comprising of 2-iodo benzyl, 2-chloro, 6-fluoro benzyl, 2,6-dichloro benzyl, 4-chloro benzyl, 2-nitro benzyl, and 3-nitro benzyl.

In another embodiment of the invention, compounds of the present invention comprise the following structural formulae:

(1d)

3',4'-di-[O-(2''-chloro-6''-fluoro-benzyl)]-garcinol

3',4'-di-[O-(2",6"-dichloro-benzyl)]-garcinol (1e)

3',4'-di-[O-(3"-nitro-benzyl)]-garcinol (1h)

3',4'-di-[O-(4"-chloro-benzyl)]-garcinol (1f)

3',4'-di-(O-prenyl)-isogarcinol (2b)

3',4'-di-[O-(2"-nitro-benzyl)]-garcinol (1g)

In yet another embodiment of the invention, the compounds of the present invention are useful as Pgp inducers and for treatment of Alzheimer's disease.

According to another aspect of the present invention, the present invention provides a process for the preparation of the compounds of formula I and II, comprising the steps of—

(i) reacting garcinol or isogarcinol with alkyl or acyl halide in presence of a base in a solvent at a temperature ranging between 0 to 35° C. for a period of time between 0 to 60 minutes to obtain a crude mixture; and (ii) optionally purifying the crude mixture column chromatography using an eluent to obtain the compounds of claim 1.

In one embodiment, crude mixture as obtained by the process steps is purified by column chromatography using hexane:ethyl acetate as eluent to obtain the desired compounds.

In yet another embodiment, the alkyl halide is selected from group comprising of methyl halide, ethyl halide, propyl halide, isopropyl halide, n-butyl halide, isobutyl halide, isovaleryl halide, propargyl halide, allyl halide, prenyl halide, geranyl halide, and halides of other long aliphatic chains with chain length from $C_5$-$C_{20}$, and acyl halide is selected from the group comprising of acetyl halide, benzyl halide, benzoyl halide and butanoyl halide.

In yet another embodiment, the alkyl halide or acyl halide is selected from the group comprising Butanoyl chloride, 2-iodo benzyl chloride, 2-chloro, 6-fluoro benzyl chloride, 2,6-dichloro benzyl chloride, 4-chloro benzyl chloride, 2-nitro benzyl chloride, 3-nitro benzyl bromide, and prenyl bromide.

In another embodiment of the invention, base is selected from group comprising of $K_2CO_3$, $Cs_2CO_3$ and $Na_2CO_3$.

In yet another embodiment of the invention, solvent is selected from group comprising of acetone, methanol, ethyl acetate, hexane, n-butanol, ethanol and propanol.

Another aspect of the present invention provides that compounds of the present invention are potent Pgp inducers.

In one embodiment, the compound 1b, 1g and 2b displayed an $EC_{50}$ of 8.9, 6.8 and 2.9 nM respectively.

Yet another aspect of the present invention provides a pharmaceutical composition for the treatment of Alzheimer's disease comprising; an effective amount of the compound of general formulae I, or II optionally along with the pharmaceutically acceptable excipients such as diluents, binders, preservatives, sweeteners, coloring agents etc.

In another embodiment of the invention, the pharmaceutically acceptable excipients are selected from a group comprising saccharides (such as lactose, starch, dextrose), stearates (such as stearic acid, magnesium stearate), polyvinyl pyrrolidine, dicalcium phosphate dihydrate, eudragit polymers, celluloses, polyethylene glycol, polysorbate 80, sodium lauryl sulfate, magnesium oxide, silicon dioxide, carbonates (such as sodium carbonate), talc.

Another embodiment of the present invention provides a method of treatment of patients, including humans afflicted with Alzheimer's disease comprising administering the compounds of claim 1 alone or in combination with other medicinal agents.

Other medicinal agents that may be combined with the compounds of the present invention in the treatment of Alzheimer's disease include but are not limited to donepezil, tacrine, rivastigmine, galantamine, memantine, and other anti-alzheimer agents.

In one aspect of the present invention, use of the compounds of general formulae I and II is provided as P-glycoprotein inducers.

Figure 1:
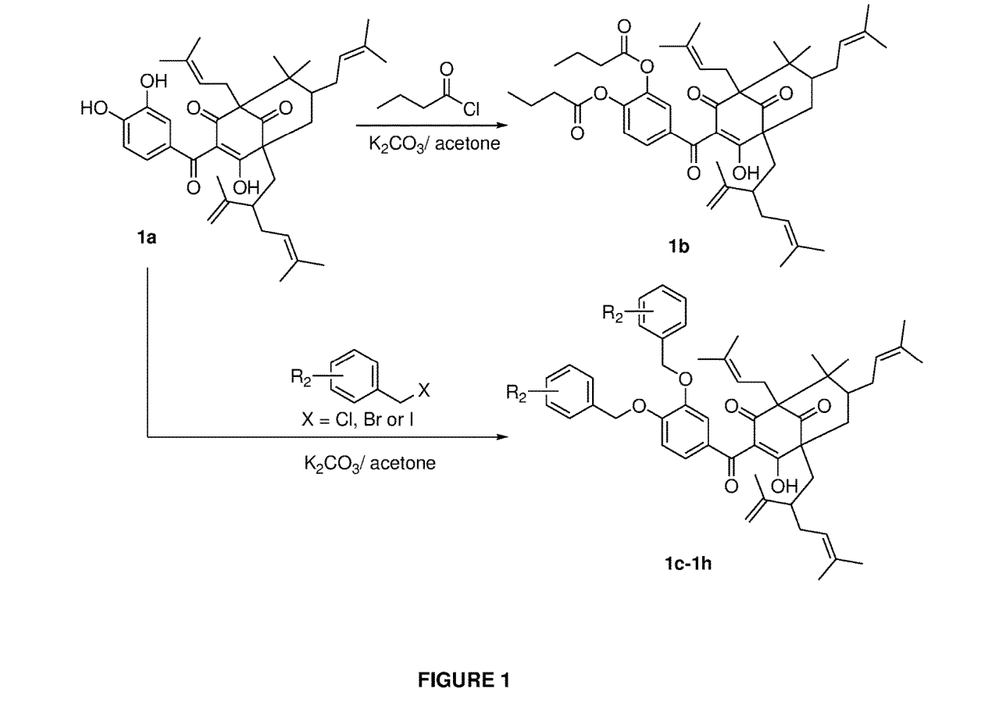
FIG. 1 is a diagram illustrating the chemical synthesis of compounds formula I
Figure 2:
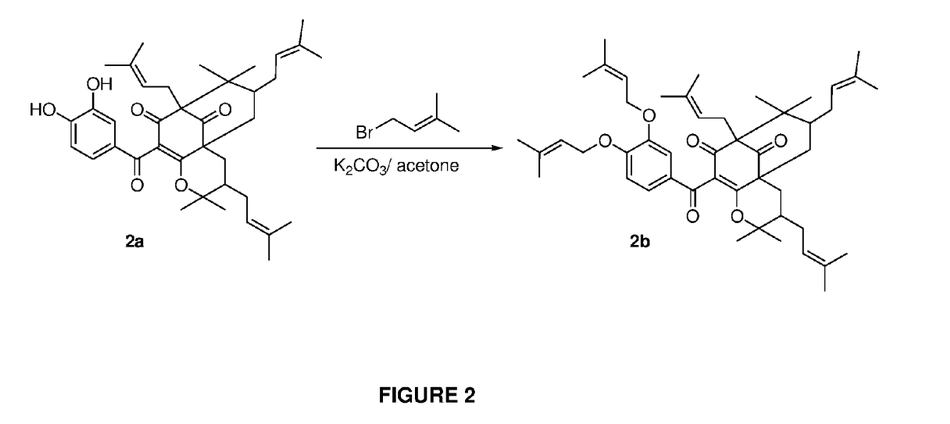
FIG. 2 is a diagram illustrating the chemical synthesis of compounds formula II
Figure 3:
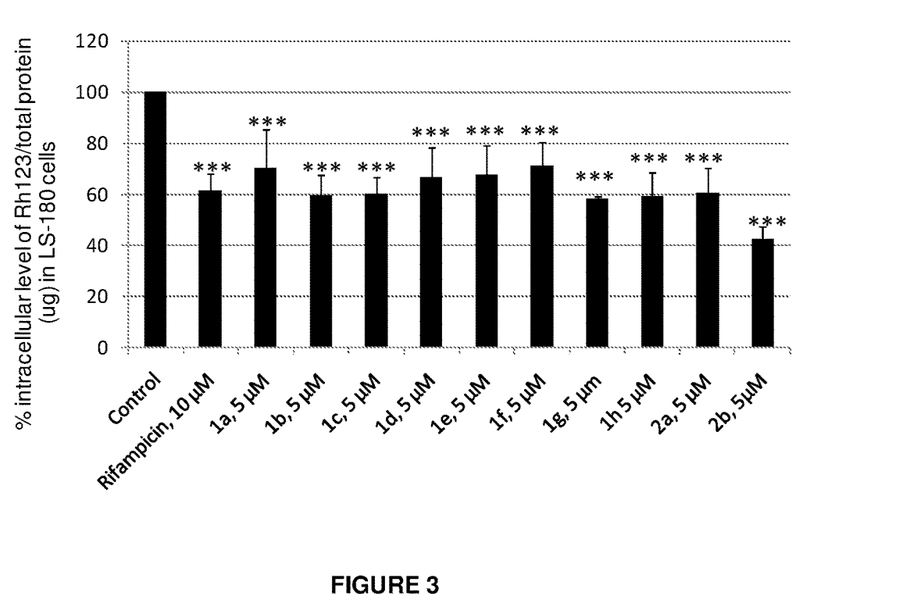
FIG. 3 is a diagram illustrating the Pgp induction activity of compounds claimed in the invention.

The present invention discloses novel polyprenylated alkyl and acyl phloroglucinol compounds which show potent p-glycoprotein induction activity. Results are shown in FIG. 3. Compounds 1b and 1g showed better Pgp induction activity compared to its parent natural product garcinol (1a) (Table 1). Similarly, compound 2b displayed better Pgp induction activity compared with its parent natural product isogarcinol (2a) (Table 2).

As the cytotoxicity is not desired for compound to be used as anti-Alzheimer agent. Therefore, the cytotoxicity of natural products garcinol (1a), isogarcinol (2a) along with synthesized new compounds was also investigated in LS-180 cells. Results are summarized in Table 1 and 2. As depicted in Table 1, the new compound 1g is devoid of cytotoxicity ($IC_{50}$>100 μM), whereas the parent natural product 1a is cytotoxic ($IC_{50}$=20 μM). The isogarcinol derivative 2b which is the most potent potent Pgp-inducer amongst all claimed compounds also was found to be less cytotoxic ($IC_{50}$=40 μM) in LS180 cells compared with its parent natural product isogarcinol (2a) ($IC_{50}$ 11 μM) (Table 2). The improved cytotoxicity profile is the major advantage of new compounds claimed in the present invention over garcinol and isogarcinol.

As used herein, the terms below have the meanings indicated.

The phrase 'therapeutically effective' is intended to qualify the amount of active ingredients used in the treatment of a disease or disorder. This amount will achieve the goal of reducing or eliminating the disease or disorder.

As used herein, reference to treatment of a patient is intended to include prophylaxis. The term patient means all mammals including humans. Examples of patients include humans, and rodents (e.g., rats, mice, and guinea pigs).

The compounds of the invention can be used to treat a patient (e.g. a human) that suffers from or is at a risk of suffering from a disease, disorder, condition, or symptom described herein. The compounds of the invention can be used alone or in combination with suitable excipients in treating or preventing Alzheimer's disease. Each such treatment described above includes the step of administering to a patient in need thereof a therapeutically effective amount of the compound of the invention described herein to delay, reduce or prevent such a disease, disorder, condition, or symptom.

It is understood that the foregoing and the following examples are merely illustrative of the present invention. It is possible that certain modifications of the articles and/or methods employed may be made and still the objectives of the invention can be achieved. Such modifications are contemplated as within the scope of the claimed invention.

EXAMPLES

Example 1: Isolation of Garcinol (1a) and Isogarcinol (2a)

The fruits of *Garcinia indica* Choisy were collected from Khari-Baoli herbal drug market of New Delhi and were authenticated by botanist of our institute. Air dried powdered fruits Choisy (4.5 g) were then extracted with dichloromethane:methanol (1:1, 10 L, 3 times, 24 h) at room temperature. The extract was concentrated to dryness using high vacuum at 40° C. to yield 900 g of dried extract. The extract (900 g) was subjected to silica gel column chromatography (EtOAc/hexane—0:100 to 20:80) to yield two major fractions, one eluted at 15% EtOAC:Hexane (fraction A) and another eluted at 20% EtOAc:hexane (fraction B). Solvent was evaporated from these fractions to yield yellow colored solids. Hexane washing of these solids obtained from fractions A and B, produced pure compounds 1a (49.2 g, yellow solid) and 2a (8.1 g, white solid). These compounds were characterized using melting point, optical rotation, $^1H$, $^{13}C$, DEPT-135 NMR and MS analysis. Based on comparison of physical and spectroscopic data with literature values, compounds 1a and 2a were characterized as garcinol (1a) and isogarcinol (2a). Spectral data of garcinol (1a): Yellow solid; $R_f$ 0.46 (15% EtOAc:hexane); m.p. 132-134° C.; $[\alpha]_D$-15.2 (c 0.1, MeOH); $^1H$ NMR (400 MHz, CDCl$_3$, ppm): δ 6.95 (m, 1H), 6.63 (m, 1H), 6.23 (m, 1H), 5.10-5.00 (m, 2H), 4.92-4.75 (m, 2H), 4.41 (d, J=17.2 Hz, 1H), 2.75 (m, 2H), 2.59-2.52 (m, 1H), 2.38-2.32 (m, 1H), 2.20-1.40 (m, 8H), 1.75 (s, 3H), 1.72 (s, 3H), 1.69 (s, 3H), 1.65 (s, 3H), 1.58 (s, 3H), 1.53 (s, 3H), 1.51 (s, 3H), 1.14 (s, 3H), 1.01 (s, 3H); $^{13}C$ NMR (100 MHz, CDCl$_3$, ppm): δ 209.1, 198.9, 194.9, 193.8, 149.7, 148.1, 143.5, 135.3, 133.0, 132.0, 127.8, 124.1, 123.8, 123.5, 120.1, 116.5, 116.3, 114.3, 112.7, 69.7, 57.9, 49.6, 46.8, 43.6, 42.6, 36.2, 32.6, 28.9, 27.0, 26.4, 26.1, 25.9, 22.7, 18.2, 18.0, 17.9, 17.6; IR (CHCl$_3$): $\nu_{max}$ 3391, 2970, 2920, 1727, 1638, 1602, 1441, 1289, 1116 cm$^{-1}$; ESI-MS: m/z 603.37 [M+1]$^+$; HRMS: m/z 603.3658 (ESI) calcd for $C_{38}H_{51}O_6$+H$^+$ (603.3680). Spectral data of isogarcinol (2a): White solid; $R_f$ 0.42 (20% EtOAc:hexane); m.p. 242-244° C.; $[\alpha]_D$-19.6 (c 0.1, MeOH); $^1H$ NMR (400 MHz, DMSO-d$_6$, ppm): δ 7.14

(s, 1H), 6.85 (dd, J=8.4, 2.0 Hz, 1H), 6.74 (d, J=8.0 Hz, 1H), 5.17 (t, J=5.0 Hz, 1H), 4.91 (t, J=5 Hz, 1H), 4.77 (t, J=5.0 Hz, 1H), 2.88 (dd, J=14.0, 3.6 Hz, 1H), 2.60-2.52 (m, 1H), 2.32 (m, 1H), 2.13 (d, J=14.8 Hz, 1H), 2.02-1.98 (m, 3H), 1.80-1.31 (m, 5H), 1.75 (s, 3H), 1.66 (s, 3H), 1.60 (s, 3H), 1.59 (s, 3H), 1.52 (s, 3H), 1.50 (s, 3H), 1.21 (s, 3H), 1.08 (s, 3H), 0.91 (s, 3H), 0.85 (s, 3H); $^{13}$C NMR (100 MHz, CDCl$_3$, ppm): δ 206.4, 193.3, 191.4, 170.4, 150.9, 145.2, 132.7, 132.5, 131.9, 128.8, 125.1, 124.8, 121.9, 120.5, 115.2, 114.9, 86.3, 67.5, 50.6, 45.5, 45.2, 42.2, 38.2, 29.0, 28.7, 28.3, 27.5, 26.1, 25.7, 25.6, 25.5, 25.0, 22.0, 20.9, 17.9; IR (CHCl$_3$): $v_{max}$ 3368, 2975, 2925, 1728, 1667, 1595, 1440, 1349, 1372, 1291, 1122, 1018 cm$^{-1}$; ESI-MS: m/z 602.37 [M]$^+$.

Example 2: Synthesis of 3',4'-Di-(O-Butanoyl)-Garcinol (1b)

To the solution of garcinol (1a, 1 mmol) in acetone was added potassium carbonate (1 mmol) and was stirred for 5 min at room temperature. Acyl halide (butanoyl chloride 1.2 mmol) was added and the reaction mixture was then stirred at room temperature for 2 hrs. Solvent was evaporated and ethyl acetate was added to the crude residue. Ethyl acetate layer was washed with water and brine solution. Organic layer was finally dried over anhydrous sodium sulphate and obtained crude product was purified by silica gel column chromatography (EtOAc:hexane—20:80) to get desired product 1b. Yellow semisolid; $^1$H NMR (400 MHz, CDCl$_3$, ppm): δ 7.62 (m, 2H), 7.36 (d, J=6.8 Hz, 1H), 5.34-5.04 (m, 2H), 4.83-4.63 (m, 2H), 4.42 (s, 1H), 2.70 (d, J=12.8 Hz, 2H), 2.54 (t, J=7.2 Hz, 6H), 2.36 (d, J=13.2 Hz, 6H), 2.02-1.87 (m, 24H), 1.79-1.74 (m, 5H), 1.66-1.55 (m, 11H); $^{13}$C NMR (100 MHz, CDCl$_3$, ppm): δ 208.9, 197.9, 193.4, 192.5, 170.3, 170.1, 148.1, 145.6, 141.7, 134.8, 132.8, 131.9, 127.8, 124.2, 123.9, 122.6, 120.4, 116.0, 112.6, 67.7, 61.7, 57.6, 49.6, 46.7, 43.5, 42.8, 36.6, 35.9, 33.7, 32.6, 31.9, 29.6, 29.5, 29.3, 29.1, 27.1, 26.2, 25.6, 24.7, 22.6, 22.5, 18.3, 17.9, 17.7, 14.0, 13.6; IR (CHCl$_3$): $v_{max}$ 2967, 2925, 2877, 1773, 1727, 1550, 1422, 1394, 1258, 1136 cm$^{-1}$; ESI-MS: m/z 743.5963 [M+H]$^+$; HRMS: m/z 743.4513 (ESI) calcd for C$_{46}$H$_{62}$O$_8$+H$^+$ (743.4517).

Example 3: Synthesis of 3',4'-di-[O-(2"-iodo-benzyl)]-garcinol (1c)

Procedure similar to example 2 except corresponding 2-iodobenzyl bromide is used. Yellow semisolid; $^1$H NMR (400 MHz, CDCl$_3$, ppm): δ 7.86 (d, J=7.6 Hz, 2H), 7.63 (d, J=6.8 Hz, 1H), 7.52 (d, J=6.8 Hz, 1H), 7.42 (s, 3H), 7.36-7.31 (m, 3H), 7.11-7.08 (m, 1H), 5.19 (m, 5H), 5.15 (s, 2H), 4.42 (d, J=10.0 Hz, 2H), 2.70 (s, 2H), 2.32 (s, 1H), 2.12-2.06 (m, 1H), 2.04-1.91 (m, 6H), 1.90-1.30 (m, 18H), 1.25-1.04 (m, 6H), 0.97-0.85 (m, 6H); $^{13}$C NMR (125 MHz, CDCl$_3$, ppm): δ 209.1, 196.8, 193.9, 192.5, 152.7, 148.1, 138.5, 132.7, 131.8, 129.6, 129.4, 128.9, 128.6, 128.5, 128.3, 125.6, 124.0, 122.7, 120.5, 115.3, 112.4, 97.1, 96.6, 75.4, 74.7, 69.6, 57.5, 43.6, 42.6, 36.6, 32.6, 29.7, 29.0, 27.0, 26.2, 25.7, 22.5, 18.2, 17.9, 17.7, 14.1; IR (CHCl$_3$): $v_{max}$ 3400, 2922, 2854, 1726, 1658, 1510, 1435, 1383, 1266, 1013, 772.6 cm$^{-1}$; ESI-MS: m/z 1035.2939 [M+1]$^+$; HRMS: m/z 1035.5412 (ESI) calcd for C$_{52}$H$_{60}$I$_2$O$_6$+H$^+$ (1035.2552).

Example 4: Synthesis of 3',4'-di-[O-(2"-chloro-6"-fluoro-benzyl)]-garcinol (1d)

Procedure similar to example 2 except corresponding 2-chloro-6-Fluoro benzyl chloride is used. Yellow semi-solid; $^1$H NMR (400 MHz, CDCl$_3$, ppm): δ 7.48 (m, 1H), 7.24-7.19 (m, 5H), 7.00 (s, 3H), 5.28-5.19 (m, 4H), 5.05 (t, J=16.0 Hz, 2H), 4.88 (s, 1H), 4.44 (d, J=12 Hz, 2H), 2.72 (t, J=8.8 Hz, 2H), 2.37-2.33 (m, 1H), 2.12-1.88 (m, 6H), 1.75-1.67 (m, 18H), 1.60-1.51 (m, 2H), 1.42 (d, J=3.2 Hz, 2H), 1.31-1.25 (m, 6H), 1.12-0.86 (m, 1H); $^{13}$C NMR (100 MHz, CDCl$_3$, ppm): δ 209.3, 197.0, 194.0, 192.6, 153.6, 148.6, 136.6, 134.6, 132.7, 131.8, 130.8, 130.7, 130.6, 130.5, 129.9, 125.8, 125.5, 122.4, 122.1, 121.9, 120.5, 117.1, 116.0, 69.7, 63.0, 62.3, 57.6, 49.5, 46.8, 43.6, 36.1, 32.6, 29.0, 27.0, 26.1, 25.7, 22.6, 18.2, 17.9, 17.7; IR (CHCl$_3$): $v_{max}$ 3433, 2967, 2923, 1725, 1658, 1597, 1455, 1375, 1265, 1007, 871, 780, cm$^{-1}$; ESI-MS: m/z 887.6218 [M+1]$^+$; HRMS: m/z 887.3650 (ESI) calcd for C$_{52}$H$_{58}$Cl$_2$F$_2$O$_6$+H$^+$ (887.3651).

Example 5: Synthesis of 3',4'-di-[O-(2",6"-dichloro-benzyl)]-garcinol (1e)

Procedure similar to example 2 except corresponding 2,6-dichloro benzyl chloride is used. Yellow semisolid; $^1$H NMR (400 MHz, CDCl$_3$, ppm): δ 7.50 (s, 1H), 7.30-7.20 (m, 6H), 6.97 (d, J=8.4 Hz, 2H), 5.37-5.29 (m, 4H), 5.05-4.88 (m, 2H), 4.69 (s, 2H), 4.42 (s, 1H), 2.72-2.34 (m, 2H), 2.06-1.92 (m, 2H), 1.74-1.67 (m, 1H), 1.56 (t, J=10.0 Hz, 6H), 1.42-1.30 (m, 29H); $^{13}$C NMR (100 MHz, CDCl$_3$, ppm): δ 209.5, 197.4, 194.0, 192.7, 153.9, 148.8, 148.2, 137.2, 137.1, 134.7, 132.9, 132.0, 131.9, 131.6, 130.6, 130.4, 128.3, 125.9, 124.2, 122.7, 120.6, 116.9, 113.4, 112.6, 69.8, 66.8, 66.3, 57.6, 49.6, 46.9, 43.6, 42.7, 36.1, 32.7, 29.0, 27.1, 26.3, 26.2, 25.9, 25.8, 22.6, 18.3, 18.0, 17.8; IR (CHCl$_3$): $v_{max}$ 3435, 2921, 1726, 1658, 1438, 1262, 1196, 1137, cm$^{-1}$; ESI-MS: m/z 919.3375 [M+1]$^+$; HRMS 919.3045 (ESI) calcd for C$_{52}$H$_{58}$Cl$_4$O$_6$+H$^+$ (919.306).

Example 6: Synthesis of 3',4'-di-[O-(4"-chloro-benzyl)]-garcinol (1f)

Procedure similar to example 2, except corresponding 4-chloro benzyl bromide is used. Yellow semisolid; $^1$H NMR (400 MHz, CDCl$_3$, ppm): δ 7.38-7.31 (m, 9H), 7.09-7.07 (m, 1H), 6.76 (d, J=8.4 Hz, 1H), 5.14 (t, J=12.4 Hz, 6H), 5.09-5.05 (m, 2H), 4.41 (d, J=10.4 Hz, 1H), 2.72 (d, J=8.8 Hz, 2H), 2.32 (s, 1H), 2.11-2.02 (m, 1H), 1.91 (d, J=4.0 Hz, 6H), 1.88-1.51 (m, 18H), 1.49-1.19 (m, 6H), 1.09-0.98 (m, 6H); $^{13}$C NMR (100 MHz, CDCl$_3$, ppm): δ 209.7, 197.1, 194.1, 192.7, 153.0, 148.2, 135.3, 134.9, 133.8, 132.7, 128.6, 125.3, 122.7, 120.6, 116.0, 115.3, 70.9, 70.3, 69.7, 57.5, 49.5, 46.5, 43.6, 36.1, 32.7, 27.0, 26.2, 25.7, 22.7, 18.2, 17.9, 17.7, 14.1; IR (CHCl$_3$): $v_{max}$ 3400, 2963, 2923, 1726, 1657, 1598, 1510, 1375, 1268, 1091, 1015, 809 cm$^{-1}$; ESI-MS: m/z 851.3774 [M+1]$^+$; HRMS: m/z 851.3835 (ESI) calcd for C$_{52}$H$_{60}$Cl$_2$O$_6$+H$^+$ (851.384).

Example 7: Synthesis of 3',4'-di-[O-(2"-nitro-benzyl)]-garcinol (1g)

Procedure similar to example 2 except corresponding 2-nitro benzyl chloride is used. Yellow semisolid; $^1$H NMR (400 MHz, CDCl$_3$, ppm): δ 8.17-8.15 (m, 2H), 8.01-7.99 (m, 2H), 7.91-7.90 (m, 2H), 7.69-7.44 (m, 3H), 7.14 (d, J=8.4 Hz, 1H), 6.83 (d, J=8.4 Hz, 1H), 5.65 (m, 4H), 5.59 (s, 2H), 5.04-4.87 (m, 1H), 4.82-4.70 (m, 1H), 4.42 (d, J=8.4 Hz, 1H), 2.72-2.33 (m, 2H), 2.11-1.88 (m, 2H), 1.71-1.50 (m, 9H), 1.42-1.20 (m, 18H), 1.10-0.98 (m, 9H); $^{13}$C NMR (100 MHz, CDCl$_3$, ppm): δ 209.6, 197.2, 194.0, 192.8, 152.4, 148.2, 147.9, 147.0, 146.9, 134.6, 134.2, 134.0, 133.6, 133.1, 132.9, 131.9, 130.1, 128.8, 128.6, 128.5, 125.7, 125.0, 125.0, 124.0, 122.7, 120.6, 116.1, 115.3, 112.5, 112.3, 69.7, 68.4, 67.7, 57.5, 49.5, 46.8, 43.6, 42.6, 36.0, 32.7, 29.7, 29.0, 27.0, 26.3, 26.2, 25.8, 25.8, 22.7, 22.6, 18.2, 18.0, 17.7; IR (CHCl$_3$): $v_{max}$ 3400, 2963, 2855, 1726, 1658, 1527, 1341, 1266, 728 cm$^{-1}$; ESI-MS: m/z 873.4612 [M+1]$^+$; HRMS: m/z 873.4283 (ESI) calcd for C$_{52}$H$_{60}$N$_2$O$_{10}$+H$^+$ (873.4321).

Example 8: Synthesis of 3',4'-di-[O-(3"-nitro-benzyl)]-garcinol (1h)

Procedure similar to example 2 except corresponding 3-nitro benzyl chloride is used. Yellow semisolid; $^1$H NMR (400 MHz, CDCl$_3$, ppm): δ 8.69-8.61 (m, 4H), 8.35 (s, 2H), 8.19 (s, 1H), 7.95-7.81 (m, 3H), 7.59-7.32 (m, 1H), 5.24 (d, J=12.4 Hz, 5H), 4.87 (d, J=16 Hz, 3H), 4.40 (s, 2H), 2.70 (s, 2H), 2.55 (d, J=10.0 Hz, 1H), 2.33-2.20 (m, 5H), 2.04-1.90 (m, 21H), 1.74-1.50 (m, 10H); $^{13}$C NMR (100 MHz, CDCl$_3$, ppm): δ; 209.2, 196.9, 194.0, 193.8, 152.5, 148.5, 148.3, 138.9, 138.4, 133.0, 132.9, 131.9, 129.9, 129.7, 125.6, 124.1, 123.2, 123.0, 122.7, 122.1, 121.9, 120.8, 115.1, 112.4, 112.3, 70.0, 69.7, 69.6, 57.5, 53.4, 49.5, 46.8, 43.6, 42.6, 36.1, 32.7, 29.7, 29.1, 27.0, 26.2, 25.7, 22.6, 18.2, 17.9, 17.7; IR (CHCl$_3$): $v_{max}$ 3400, 2922, 2853, 1726, 1657, 1531, 1384, 1269, 772 cm$^{-1}$; ESI-MS: m/z 873.4664 [M+1]$^+$; HRMS 873.4305 (ESI) calcd for C$_{52}$H$_{60}$N$_2$O$_{10}$+H$^+$ (873.4321).

Example 9: Synthesis of 3',4'-di-(O-prenyl)-isogarcinol (2b)

Procedure similar to example 2 except corresponding prenyl bromide is used. Pale yellow sticky liquid; $^1$H NMR (400 MHz, CDCl$_3$): δ 7.34 (s, 1H), 7.25-7.24 (d, J=4.0 Hz, 1H), 6.80 (d, J=8.0 Hz, 1H), 5.67 (s, 1H), 5.45 (s, 1H), 5.21 (s, 1H), 4.92 (s, 2H), 4.61 (d, J=4.0 Hz, 2H), 3.06 (d, J=12.0 Hz, 1H), 2.69 (d, J=12.0 Hz, 2H), 2.44 (d, J=12.0 Hz, 1H), 2.29 (d, J=12.0 Hz, 2H), 1.77 (d, J=8.0 Hz, 4H), 1.69-1.59 (m, 15H), 1.42 (s, 9H), 1.26 (d, J=8.0 Hz, 12H), 1.16 (s, 4H), 0.97-0.88 (m, 6H); $^{13}$C NMR (100 MHz, CDCl$_3$, ppm): δ 207.3, 193.9, 192.5, 171.1, 150.0, 145.6, 139.4, 134.5, 133.6, 133.1, 131.2, 125.4, 125.0, 122.5, 121.4, 119.9, 118.7, 114.6, 110.8, 86.3, 51.2, 46.3 46.2, 42.7, 39.4, 29.7, 29.6, 29.3, 28.8, 28.4, 26.8, 26.1, 26.0, 25.8, 25.7, 25.6, 22.7, 22.5, 21.3, 18.3, 18.0; IR (CHCl$_3$): $v_{max}$ 3434, 2969, 2924, 1727, 1643, 1674, 1594, 1426, 1264, 1122 cm$^{-1}$; ESI-MS: m/z 739.200 [M]$^+$.

Example 10: Pgp-Induction Assay

All synthesized compounds were screened for their ability to induce Pgp by using rhodamine123 (Rh123) cell exclusion method. In this method, the Pgp function was evaluated in terms of rhodamine 123 (Rh123) accumulations and efflux. Briefly, the protocol used is as follows: Colorectal LS180 cells Colorectal LS-180 cells [obtained from ECACC (European Collection of Cell Cultures) catalogue number: 87021202; passage number 52] were seeded at a density of 2×10$^4$ per well of 96 well plate and were allowed to grow for next 24 h. Cells were further incubated with the test compounds, and were diluted to a final concentration of 100 nM and rifampicin (standard) to a final concentration of 10 μM in complete media for 48 h. The final concentration of DMSO was kept at 0.1%. Drugs were removed and cells were incubated with HANKS buffer for 40 minutes before further incubation with HANKS buffer (containing 10 μM of Rh123 as a Pgp substrate) for 90 minutes. At the end of Rh123 treatment cells were washed four times with cold PBS followed by cell lysis for 1 h by using 200 μl of lysis buffer (0.1% Triton X-100 and 0.2 N NaOH). A total of 100 μl of lysate was used for reading fluorescence of Rh123 at 485 nm/529 nm. Samples were normalized by dividing fluorescence of each sample with total protein present in the lysate. All new polyprenylated phloroglucinol compounds that showed potent p-glycoprotein induction activity (results are shown in FIG. 3). For EC$_{50}$ determination, different concentrations of compound were used to treat LS180 cells for 48 h. EC$_{50}$ was determined by plotting fluorescence of Rh123 against concentration of compound. EC$_{50}$ values are shown in Table 1 and 2. Compounds 1b, 1g and 2b showed better Pgp induction activity compared to their parent natural products.

TABLE 1

Pgp induction EC$_{50}$ and cytotoxicity IC$_{50}$ values for garcinol (1a) and compounds 1b and 1g in LS-180 cells

| Compound | Pgp induction EC$_{50}$ (μM) | Cytotoxicity IC$_{50}$ (μM) |
| --- | --- | --- |
| Garcinol (1a) | 0.012 | 20 |
| 1b | 0.0089 | ND |
| 1g | 0.0068 | >100 |

ND: not determined.

TABLE 2

Pgp induction EC$_{50}$ and cytotoxicity IC$_{50}$ values for isogarcinol (2a) and compound 2b in LS-180 cells

| Compound | Pgp induction EC$_{50}$ (μM) | Cytotoxicity IC$_{50}$ (μM) |
| --- | --- | --- |
| Isogarcinol (2a) | 0.0070 | 11 |
| 2b | 0.0029 | 40 |

Compounds 1b and 1g showed better Pgp induction activity compared to its parent natural product garcinol (1a) (Table 1). Similarly, compound 2b displayed better Pgp induction activity compared with its parent natural product isogarcinol (2a) (Table 2).

Example 11: Cytotoxicity of Compounds of the Invention

Compounds proposed in present invention were evaluated for their cytotoxic effect in LS-180 cells using MTT assay. In each well of a 96-well plate, 3×10$^3$ cells were grown in 100 μL of medium. After 24 h, each test molecules were added to achieve a final concentration of 10 to 0.01 μmol/L, respectively. After 48 h of treatment, 20 μL of 2.5 mg/mL MTT solution in phosphate buffer saline was added to each well. After 48 h, supernatant was removed and formazan crystals were dissolved in 200 μL of DMSO. Absorbance was then measured at 570 nm using an absorbance plate reader. Data are expressed as the percentage of viable cells in treated relative to non-treated conditions. Each experiment was repeated thrice and data was expressed as mean±SD of three independent experiments (Mordant, P. et al., Mol. Cancer Ther. 2010, 9, 358).

As the cytotoxicity is not desired for compound to be used as anti-Alzheimer agent, therefore, the cytotoxicity of natural products garcinol (1a), isogarcinol (2a) along with synthesized new compounds was investigated in LS-180 cells. Results are summarized in Table 1 and 2. As depicted in

Table 1-2, new compounds 1g and 2b are less cytotoxicity (IC$_{50}$>100 and 40 μM, respectively) showing huge selectivity index with respect to Pgp induction activity. The compound 1g which exhibits potent Pgp-induction activity (EC$_{50}$=6.8 nM) is completely devoid of cytotoxic activity (IC$_{50}$>100 μM) whereas its parent natural product garcinol (1a) is cytotoxic (IC$_{50}$=20 μM). This is a major advantage of new compounds claimed in the present invention over garcinol and isogarcinol.

ADVANTAGES OF THE INVENTION

The main advantages of the present invention are:
Compounds claimed in the present invention possess potent Pgp induction activity, better than their parent natural products.
Compounds 1g and 2b as claimed in the present invention, display EC$_{50}$ of 6.8 and 2.9 nM for p-glycoprotein induction activity, better than their parent natural products.
Compounds claimed in the present invention are not cytotoxic, whereas parent natural products are cytotoxic.
Compounds of the invention are stable.

The invention claimed is:
1. A compound having a structural formulae selected from:

1b

1c

1d

1e

1f

-continued

1g

1h

2b

2. A process for the preparation of the compounds as claimed in claim 1, comprising the steps of—

(i) reacting garcinol or isogarcinol with alkyl or acyl halide in presence of a base in a solvent at a temperature ranging between 0 to 35° C. for a period of time between 0 to 60 minutes to obtain a crude mixture; and (ii) optionally purifying the crude mixture column chromatography using an eluent to obtain the compounds of claim 1.

3. The process as claimed in claim 2 wherein the alkyl halide is selected from group comprising of methyl halide, ethyl halide, propyl halide, isopropyl halide, n-butyl halide, isobutyl halide, isovaleryl halide, propargyl halide, allyl halide, prenyl halide, geranyl halide, and halides of other long aliphatic chains with chain length from C5-C20, and acyl halide is selected from the group comprising of acetyl halide, benzyl halide, benzoyl halide and butanoyl halide.

4. The process as claimed in claim 2 wherein the alkyl halide or acyl halide is selected from the group comprising Butanoyl chloride, 2-iodo benzyl chloride, 2-chloro, 6-fluoro benzyl chloride, 2,6-dichloro benzyl chloride, 4-chloro benzyl chloride, 2-nitro benzyl chloride, 3-nitro benzyl bromide, and prenyl bromide.

5. The process as claimed in claim 2 wherein base is selected from group comprising of K2CO3, Cs2CO3 and Na2CO3.

6. The process as claimed in claim 2 wherein solvent is selected from group comprising of acetone, methanol, ethyl acetate, hexane, n-butanol, ethanol and propanol.

7. The compound as claimed in 1, claim wherein compound 1b, 1g and 2b displayed $EC_{50}$ of 8.9, 6.8 and 2.9 nM respectively.

8. A pharmaceutical composition for the treatment of Alzheimer's disease comprising; an effective amount of the compound as claimed in claim 1, optionally along with the pharmaceutically acceptable excipients.

9. The composition as claimed in claim 8 wherein the pharmaceutically acceptable excipient is selected from a group comprising saccharides, stearates, polyvinyl pyrrolidine, dicalcium phosphate dihydrate, eudragit polymers, celluloses, polyethylene glycol, polysorbate 80, sodium lauryl sulfate, magnesium oxide, silicon dioxide, carbonates, and talc.

10. A method of treatment of patients, including humans afflicted with Alzheimer's disease comprising administering the compounds of claim 1 alone or in combination with other medicinal agents.

* * * * *